(12) United States Patent
Martyak et al.

(10) Patent No.: US 9,399,618 B2
(45) Date of Patent: Jul. 26, 2016

(54) HIGH PURITY ELECTROLYTIC SULFONIC ACID SOLUTIONS

(75) Inventors: Nicholas M. Martyak, Doylestown, PA (US); Martin Nosowitz, Paoli, PA (US); Gary S. Smith, Collegeville, PA (US); Patrick Kendall Janney, Ridley Park, PA (US); Jean-Marie Ollivier, Buzy (FR)

(73) Assignee: Arkema Inc., King of Prussia, PA (US)

( * ) Notice: Subject to any disclaimer, the term of this patent is extended or adjusted under 35 U.S.C. 154(b) by 730 days.

(21) Appl. No.: 13/069,939

(22) Filed: Mar. 23, 2011

(65) Prior Publication Data

US 2011/0198227 A1    Aug. 18, 2011

Related U.S. Application Data

(63) Continuation-in-part of application No. 10/555,362, filed as application No. PCT/US2004/012887 on Apr. 27, 2004, now abandoned.

(60) Provisional application No. 60/469,764, filed on May 12, 2003.

(51) Int. Cl.
*C25D 5/00* (2006.01)
*H01G 9/02* (2006.01)
*C09K 13/00* (2006.01)
*H01M 4/88* (2006.01)
(Continued)

(52) U.S. Cl.
CPC ............ *C07C 303/44* (2013.01); *C09D 5/4476* (2013.01); *C09D 5/4484* (2013.01); *C25D 3/02* (2013.01); *C25F 1/02* (2013.01); *H01M 2300/0011* (2013.01)

(58) Field of Classification Search
CPC ............. C25D 3/00; C25D 3/12; C25D 3/20; C25D 3/22; C25D 3/38; H01M 4/36; C08G 85/00; C25F 1/04
USPC ........... 205/80, 261, 291, 295, 296, 270, 271, 205/274, 305, 311, 313; 252/62.2, 79.1, 252/182.1, 500
See application file for complete search history.

(56) References Cited

U.S. PATENT DOCUMENTS 2,383,895 A    8/1945  Stareck et al.
3,770,598 A    11/1973 Creutz
(Continued)

FOREIGN PATENT DOCUMENTS

DE    4338148    5/1995
EP    0505692    9/1992
(Continued)

OTHER PUBLICATIONS

Gernon, M.D., et al., Environmental Benefits of Methanesulfonic Acid: Comparative Properties and Advantages, Green Chemistry, Jun. 1999, pp. 127-140.
(Continued)

*Primary Examiner* — Edna Wong
(74) *Attorney, Agent, or Firm* — Steven D. Boyd

(57) ABSTRACT

Disclosed is a solution for an electrochemical process, the solution containing a sulfonic acid and having a low concentration of sulfur compounds, either low or high valence, that are susceptible to reduction and which is intended for use in electrodeposition, batteries, conductive polymers and descaling processes.

24 Claims, 1 Drawing Sheet

(51) Int. Cl.
*H01B 1/00* (2006.01)
*H01B 1/12* (2006.01)
*C07C 303/44* (2006.01)
*C09D 5/44* (2006.01)
*C25D 3/02* (2006.01)
*C25F 1/02* (2006.01)

(56) References Cited

U.S. PATENT DOCUMENTS

| | | | |
|---|---|---|---|
| 3,778,357 A | 12/1973 | Dahms et al. | |
| 4,207,150 A * | 6/1980 | Creutz et al. | 205/310 |
| 4,374,709 A | 2/1983 | Combs | |
| 4,376,785 A | 3/1983 | Matsuo et al. | |
| 4,555,315 A | 11/1985 | Barbieri et al. | |
| 4,673,469 A | 6/1987 | Beach et al. | |
| 4,895,977 A | 1/1990 | Nosowitz | |
| 5,698,830 A * | 12/1997 | Lacombe et al. | 204/157.15 |
| 6,187,169 B1 | 2/2001 | Gernon et al. | |
| 6,531,629 B1 | 3/2003 | Eiermann et al. | |
| 7,452,486 B2 | 11/2008 | Martvak et al. | |
| 2001/0053449 A1 | 12/2001 | Parekh et al. | |
| 2003/0003320 A1 * | 1/2003 | Matsuo et al. | 428/647 |
| 2007/0051925 A1 | 3/2007 | Martvak et al. | |

FOREIGN PATENT DOCUMENTS

| | | |
|---|---|---|
| JP | 07179578 A | 7/1995 |
| JP | 2000328285 A | 11/2000 |

OTHER PUBLICATIONS

Lowenheim, F., Modern Electroplating, 3rd Eddition, 1974, pp. 296-303.
Bodnevas et al.. Effect of Additive Conversion on Internal Stresses in Nickel Deposits, Dec. 1994, pp. 75-79.
Gernon et al., The Recovery of Pure Alkanesulfonic Acids From Corresponding Metal Alkanesulfonate Salts,Clean and Efficient Processing: Electrochemical Technology for Synthesis, Separations, Recycle and Emvironmental Improvement, International Forum, Electrolysis in the Chemical Industry, 12th, Clearwater Beach, Fla., Oct. 11-15, 1998, pp. 252-285.
Clarke, R.L. et al., Introducing Cerium Based High Energy Redox Batteries, EESAT Conference Paper, Apr. 15, 2002, pp. 1-6.

* cited by examiner

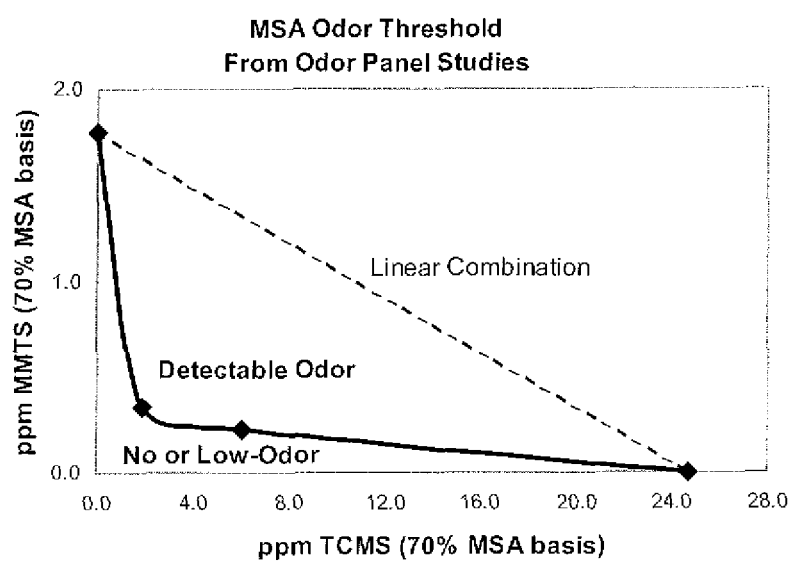

HIGH PURITY ELECTROLYTIC SULFONIC ACID SOLUTIONS

This application is a continuation-in-part application of U.S. Ser. No. 10/555,362 filed Nov. 2, 2005, now abandoned.

BACKGROUND OF THE INVENTION

1. Field of the Invention

The present invention relates to high purity sulfonic acids and their use in electrochemical processes, methods for preparing such high purity acids, methods for preparing high purity metal-sulfonate or sulfonic acid solutions, and products formed by using such methods and solutions.

2. Prior Art

Electrochemical processes may contain acid electrolytes to impart conductivity and thus lower the required voltage, aid in the dissolution of metal (e.g., formation of metal salts) and metal oxides (e.g., descaling), aid in the deposition of metals from aqueous solutions (e.g., electrodeposition), and may be used in the synthesis of conductive polymers to provide proton conduction and in batteries to aid in the dissolution and solvation of metals such as zinc and lead.

There are many acids that may be used in the above applications such as sulfuric, nitric, phosphoric, sulfamic, and hydrochloric acid as well as phosphonic and sulfonic acids. The choice of the acids is very dependent upon the application and the purity of the acid. For example, hydrochloric acid is not typically used to descale ferrous-based metals due to its propensity for pitting corrosion in the metal. Sulfuric acid is not often used in the electrodeposition of silver or lead-based alloys due to the likelihood of metal precipitation in this acid.

There are also usually several grades or purities of acids and the choice of grade is often again dependent upon the industrial application. For example, sulfuric acid may be purchased as technical grade, reagent grade, electronic grade and microelectronic grade. Technical grade has the most impurities and is therefore not used in metal electrodeposition solutions as required in the microelectronic field.

Recently, sulfonic acids, including alkane sulfonic acids, have gained acceptance in many commercial applications due in large part to (a) their ability to solubilize metals that are insoluble in acids such as sulfuric acid, are typically non-corroding acids like hydrochloric, (b) being reducing acids unlike nitric acid and (c) being more stable than sulfamic acid at low to moderate pH and elevated temperatures.

Additionally, improvements in electroplating solutions and techniques have been made (a) to meet increased standards for plating and (b) to be able to plate under more highly difficult circumstances.

Most improvements focused on the use of organic additives such as suppressor additives, accelerator additives and leveling additives and the like to obtain the desired results.

However, even with the improvements in electroplating processes, circumstances may exist that can lead to plating defects due to inadequate coverage in recess areas such as in the vias or trenches or through-holes in electronic devices, poor corrosion resistance of the deposited metal, too high a residual stress leading to cracking in the metal coating or a rough, commercially unacceptable deposit. These defects can occur as a result of an imbalance of the organic additives intended to obtain the desired metallic coating.

Also, the useful lifetime of many metal electrodeposition electrolytes is dependent upon the breakdown of the organic additives, particularly the sulfur-containing accelerator additive.

It is well known in the industry that by having typical low valent sulfur-containing accelerator type additive such as those used in acid copper, nickel, cobalt and iron solutions, uniform plating of particularly low to high aspect ratio vias and microvias and other difficult-to-plate electronic features such as through-holes in printed circuit boards is possible.

Typical accelerator or brightener additives contain one or more low valent sulfur atoms, and typically without any nitrogen atoms and a molecular weight of about 1500 or less. In all cases, the low-valent sulfur accelerator or brightener decomposes to impart the desired effects.

However, combinations of various low-valent sulfur compounds is typically unwanted due to competitive interactions at the surface of the work piece.

Therefore, it would be desirable to control the concentration of the wanted low-valent sulfur additive in narrow ranges, often in the milligram per liter range, and to avoid the interaction with unwanted low-valent sulfur impurity molecules from the acid make-up solution.

The synthesis of conductive polymers such as polyaniline may also employ sulfonic acids to impart conductivity through protonic doping. Choi and co-workers in Synthetic Metals showed aniline polymerization in the presence of dodecylbenzesulfonic acid exhibited good electrical conductivity. Dominis and co-workers in Synthetic Metals, studied the synthesis of polyaniline in a solution containing nonyl-naphthalene sulfonic acid and found that the sulfonic acid aids in the solvation of the conductive polymer in organic media. There was no mention of the purity of the sulfonic acid used in these studies.

During the electrodeposition of nickel, iron and cobalt, additives may be employed in the aqueous electroplating solution to impart brightness to the metal deposit, decrease the stress in the metal coating, increase the corrosion protection of the underlying substrate or to achieve a desired esthetic appearance.

The composition of the additives used in the electroplating solution is dependent upon the desired metal coating. However, in general, additives for these metal electroplating baths may contain sulfur moieties as described by Lowenheim in *Modern Electroplating*, $3^{rd}$ Ed. Class 1 brighteners reduce the grain size of the metal coating but also incorporate a small, about 0.03%, amount of sulfur. In the corrosion protection of steel, a duplex nickel coating is required whereby the under-lying nickel (e.g., close to the steel) must not contain any sulfur in the deposit. The nickel electrolyte is formulated such that the additives do not contain reducible sulfur compounds that may eventually be co-deposited in the nickel. The top nickel layer of the duplex contains small amounts of sulfur and corrodes preferentially compared to the underlying sulfur-free nickel coating. Bodnevas and Zahavi in *Plating and Surface Finishing*, (December 1994, pg. 75) showed the effects of sulfur-bearing additives on the internal stress of nickel deposit, the incorporation of sulfur into the nickel coating and the relationship between the sulfur-additive concentration in the solution and the incorporation of elemental sulfur in the nickel deposit plated from sulfate-based solutions. If the nickel electrolytes are made using impure sulfonic acids such as those containing reduced or easily reducible sulfur compounds, the likelihood of sulfur incorporation increases significantly thus affecting the resultant stress in the deposit, the brightness of the metallic coating and the corrosion properties.

In depositing low stress nickel coatings, for use in aerospace applications, from sulfamate-based solutions, no sulfur is co-deposited in the coating even if using a conventional sulfur-bearing stress reducing agent such as 1,3,5, naphthalenetrisulfonic acid (NTS). In NTS, sulfur has an oxidation state of +6 and is not easily reduced. However, reducible sulfur compounds, if present in impure sulfonic acids, may alter the grain size of the nickel deposit and consequentially alter the stress in the metallic nickel deposit.

The synthesis of sulfonic acids may be complex and several undesirable impurities may be present in the desired sulfonic acids leading to difficulties in using sulfonic acids in electrochemical processes. Sulfonic acids may be made via the oxidation of the corresponding thiol, by hydrolysis of alkanesulfonyl halide, or by the oxidation of dimethyldisulfide. Various impurities may also be made during the oxidation or hydrolysis reaction and thus must be removed prior to use. Many low valent sulfur compounds such as sulfur (II) or sulfur (IV) or higher valent sulfur molecules such as sulfur (VI) compounds that are susceptible to reduction and are present in the sulfonic acid may produce a stench or odor, interfere with the ongoing electrochemical process or alter the final product.

Low valent or easily reducible sulfur compounds in an acidic medium may also produce an undesired sulfur stench. This stench comes from the formation of minute amounts of hydrogen sulfide, dimethylsulfide or sulfur dioxide. These materials are unwanted and dangerous during electrochemical processes.

It thus would be desirable to have new electrochemical compositions based on high purity sulfonic acids. It would be particularly desirable to have new sulfonic acid compositions that can be effectively used with metals of strong reducing capabilities such as tin, zinc and iron without deleterious effects such as odor and defects in the metal or polymer deposit. Such compositions could be used in electrodeposition, batteries, conductive polymers and de-scaling applications.

SUMMARY OF THE INVENTION

The invention provides aqueous solutions for use in an electrochemical process. The solution comprises a sulfonic acid and low concentrations of low-valent sulfur (II) compounds and higher-valent sulfur (IV) compounds that are susceptible to reduction and that are capable of producing an unwanted odor during makeup and use and undesirable effects during electrolysis.

Compositions of the present invention are useful in processes that are tailored to meet more stringent requirements in electrodeposition of electronic circuits, conductive polymers, batteries and descaling work.

The compositions of the invention are useful for depositing a metal, modifying or cleaning a scaled metal surface or for use as acid electrolytes in batteries or during the synthesis of conductive polymers.

BRIEF DESCRIPTION OF THE DRAWINGS

FIG. 1 is a graph of odor threshold for mixtures of trichloromethyl methyl sulfone, and methyl methanethiosulfonate.

DETAILED DESCRIPTION OF THE INVENTION

Compositions of the invention suitably contain a sulfonic acid with a low concentration of reduced or easily reducible sulfur species that have the ability to produce an odor during the dissolution of a metal or interfere with the electrolysis process.

It has now been found that compositions of high purity sulfonic acids, which when employed in electrochemical processes, produce no odor during make-up and use and commercially acceptable metal deposits, cleaned metal surfaces and polymer coatings are obtained.

This invention focuses on the unexpected superiority of using high purity sulfonic acids in electrochemical processes such as in electrodeposition, batteries, conductive polymers and descaling.

The sulfonic acids used in this invention have low concentrations of reduced sulfur compounds or sulfur compounds in high oxidation states that are susceptible to reduction, that are capable of producing an undesirable odor during use, during make-up of metal-sulfonate salts. These undesirable low valent sulfur compounds are also capable of producing rough or commercially unacceptable electrodeposits produced from the metal-sulfonate salt solutions. If present in sufficiently high enough concentration, the low valent sulfur compound may be incorporated into the metallic coating and thus alter the corrosion protection of the metals. The low valent sulfur compounds may also interfere with the polymerization of organic monomers to form conductive polymers.

Sulfonic acid electrolytes of the invention are characterized in significant part by comprising a low concentration of reduced sulfur compounds or sulfur compounds in a higher oxidation state that are susceptible to reduction by an active metal or during electrolysis to low valent sulfur compounds (odor-causing impurities) such as sulfides.

In particular, preferred high purity solutions of the present invention have a total concentration of reduced sulfur compounds less than about 50 mg/liter, more preferably a total concentration of at least less than 5 mg/liter, still more preferably at least less than 1 mg/liter.

In addition, other compounds may be used with the high purity sulfonic acid solutions of the present invention, such as metal salts of the sulfonic acid or other inorganic or organic metal salts, plating additives such as grain refiners, levelers, accelerators, conductivity salts, buffers, chelating agents.

The sulfonic acids of this invention may also contain oxidizing agents, reducing agents, sequestering agents, surfactants, emulsifying agents, viscosity modifiers, wetting agents, lubricants, soaps and a co-solvent. The choice of additional additives or buffers is dependent upon the operation of choice such as electrodeposition, descaling, organic monomer polymerization, energy storage devices and mixture of the above compounds may be used to effective the desired result.

The invention also relates to the production of metal salts using the high purity sulfonic acid. Metal sulfonates solutions may be produced from a variety of processes such as the electro-dissolution of a metal into the high purity sulfonic acid, dissolution of various metal oxides, carbonates or other metal salts.

The invention also includes articles of manufacture employing sulfonic acids of this invention, including electronic packaging devices such as printed circuit boards, multichip modules, semiconductor integrated circuits, mechanical-electronic machine devices (i.e., MEMS devices) and the like, batteries such as zinc-halogen, zinc-lanthanide, and vanadium-based energy storage devices, conductive polymers such as polyaniline and polypyrrole, zinc galvanized steel, tin-plated steel, automobile parts, aerospace parts and other articles of manufacturing using the sulfonic acids described in this invention.

The high purity sulfonic acids of the present invention may be prepared whereby the impure sulfonic acid is first treated to remove the low-valent sulfur molecules by adding to the impure sulfonic acid an oxidizing agent to increase the valency of the impurity or low valent suffer molecules, mixing the sulfonic acid with the oxidizing at temperatures between 25° C. to about 95° C. for a sufficient time to complete or nearly complete the oxidation of the low valent sulfur compounds to the higher-state sulfur compounds. Optionally, one may heat the sulfonic acid to elevated temperatures to remove or destroy any residual oxidizing agent, and optionally, adding activated carbon powder to remove residual impurities remaining in the sulfonic acid.

Many different oxidizing agents may be used such as hydrogen peroxide, nitric acid, permanganate ion, an anodic electric current, monoperoxysulfate, an aqueous solution of chlorine, or a halogen in a solution of a carboxylic acid.

Sulfonic acids used in this invention contain impurities such as low valent sulfur (II) or sulfur (IV) compounds or higher valent sulfur (VI) compounds that are susceptible to reduction and may form odorous sulfur compounds. For example, dimethylsulfone, $CH_3SO_2CH_3$, maybe reduced to sulfur dioxide, $SO_2$, or dimethylsulfide (DMS), $CH_3SCH_3$. The oxidation state of sulfur in $DMSO_2$ is six whereas in $SO_2$, sulfur is in the ±four oxidation state and in DMS it is two. MMTS, $CH_3SO_2SCH_3$, which has both a sulfur(II) and a sulfur(VI) entity may be reduced by metals or electrochemically to dimethyldisulfide, $(CH_3SSCH_3)$, whereby both sulfurs are now in the +two oxidation state.

The sulfonic acid used in this invention are characterized in large part as an alkyl monosulfonic acid, an alkyl polysulfonic acid or an aryl mono or polysulfonic acid with low concentrations of reduced or easily reducible sulfur compounds and are introduced as:

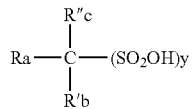

wherein a+b+c+y equals 4; R, R' and R" are the same or different and each independently may be hydrogen, phenyl, Cl, F, Br, I, $CF_3$ or a lower alkyl group such as $(CH_2)n$ where n is from 1 to 23 and that is unsubstituted or substituted by oxygen, Cl, F, Br, I, $CF_3$, —$SO_2OH$.

The preferred alkyl sulfonic acids are methanesulfonic, ethanesulfonic and propanesulfonic acids; the preferred alkyl polysulfonic acids are methanedisulfonic acid, monochloromethanedisulfonic acid, dichloromethanedisulfonic acid, 1,1-ethanedisulfonic acid, 2-chloro-1,1-ethanedisulfonic acid, 1,2-dichloro-1,1-ethanedisulfonic acid, 1,1-propanedisulfonic acid, 3-chloro-1,1-propanedisulfonic acid, 1,2-ethylene disulfonic acid, 1,3-propylene disulfonic acid, trifluormethanesulfonic acid, butanesulfonic acid, perfluorobutanesulfonic acid, and pentanesulfonic acid; and the preferred aryl sulfonic acids are phenylsulfonic, phenolsulfonic, para-toulenesulfonic, and xylenesulfonic acids; or mixtures thereof.

The sulfonic acid may be used from a concentration range from less than 1 g/l to 1480 g/l, more preferably, at a concentration of about 10 to about 700 grams per liter of solution, still more preferably, at a concentration of from about 30 to about 500 grams per liter of solution.

The sulfonic acid solution of the invention may have a pH that is between –2 to 13.

The sulfonic acid of the invention may be an aqueous solution wherein the acid solution is a mixture of a sulfonic acid with other inorganic or organic acids.

As discussed above, electroplating solutions, batteries and de-scaling formulations of the invention are particularly effective in solubilizing active metals such as tin, nickel, cobalt, iron, zinc and more noble metals such as copper and silver without the production of an unwanted odor.

Pure sulfonic acid or metal sulfonate solutions of the invention generally comprise at least one soluble metal salt, an acid electrolyte, optionally a buffering agent, optionally plating bath additives generally referred to as leveling agents, brighteners, suppressors, conductivity salts and the like, and optionally a halogen ion. More particularly, electroplating compositions of the invention preferably contain a metal salt of an alkyl or aryl sulfonic acid of this invention; an electrolyte, preferably an acidic aqueous solution such as a sulfonic acid solution with optionally a buffering agent, optionally plating bath additives generally referred to as leveling agents, brighteners, suppressors and the like, and optionally a halogen ion and the like.

A variety of metal salts may also be in the sulfonic acid electrolyte of this invention, the exact composition is dependent upon the desired final metal finish and properties of the metallic coating. Metal sulfonate salts selected from Group 1B, 2B, 3A, 3B, 4A, 4B, 5A, 5B, 6B, 7B, 8B, lanthanide and actinide metals of the periodic table and ammonium ion or mixtures thereof may be used.

Metal alkanesulfonate salts may be employed in the subject electroplating solutions wherein the alkanesulfonic acid of the anionic portion of the metal salt and any free acid are introduced as an alkyl or aryl sulfonic acid having the formula as above. The preferred alkyl sulfonic acids, alkyl polysulfonic acids and aryl sulfonic acids are as above. Metal methanesulfonates are particularly preferred metal salts.

The term metal sulfonate in this invention includes metals and metal alloys. Metals and alloys may be selected from Group 1B, 2B, 3A, 3B, 4A, 4B, 5A, 5B, 6B, 7B, and 8B, lanthanide and actinide metals of the periodic table as well as ammonium ion or mixtures thereof.

The metal salt of an alkyl or aryl sulfonic acid usually has the formula:

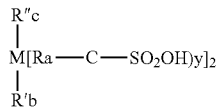

wherein a+b+c+y equals 4,
R, R' and R" are the same or different and each independently may be hydrogen, phenyl, Cl, F, Br, I, $CF_3$ or a $C_{1-9}$ alkyl group such as $(CH_2)n$ where n is from 1 to 23 and that is unsubstituted or substituted by oxygen, Cl, F, Br, I, $CF_3$, or —$SO_2OH$.

A metal sulfonate salt may be suitably present in a relatively wide concentration range in the aqueous sulfonic acid of the invention. Preferably, a metal salt will be employed at a concentration from about less than 1 grams per liter to about 500 grams per liter of plating solution, more preferably at a concentration of from about 20 to about 300 grams per liter of plating solution, still more preferably at a concentration of from about 40 to about 175 grams per liter of plating solution.

In addition, metal salts of sulfate, nitrate, sulfamate, and chloride from Group 1B, 2B, 3A, 3B, 4A, 4B, 5A, 5B, 6B, 7B, 8B, lanthanide and actinide metals of the periodic table and ammonium ion or mixtures thereof may also be used in this invention.

Preferred metal methanesulfonates are those of zinc, copper, nickel, ferrous, alkali earth metals and alkaline earth metals.

The electrolyte may also contain free acid to increase solution conductivity such as that needed in efficient batteries and electrodeposition processes. The preferred free acid has the same anion as the metal salt anion but mixtures of acids are also within the scope of this invention. Acids such as sulfuric, hydrochloric, sulfamic, acetic, propioinic, phosphonic, tartartic, oxalic, phosphonic and nitric among others may be used in this invention.

The free acid concentration ranges from about less than 1 gram per liter to about 900 gram per liter, more preferably at a concentration of from about 2 to about 700 grams per liter of plating solution, still more preferably at a concentration of from about 10 to about 500 grams per liter of solution.

The invention also includes sulfonate solutions that are substantially or completely free of added inorganic or organic acids and may be neutral or basic (e.g. pH of at least less than about 13 to about 7). Such sulfonate electrolyte compositions are suitably prepared in the same manner with the same components as other compositions disclosed herein but without an added free sulfonic acid.

Electrochemical sulfonic solutions of the invention may employ a halide ion source, particularly a chloride ion source. Examples of other suitable halides include fluoride, bromide and iodide. A wide range of halide ion concentrations (if a halide ion is employed) may be suitably utilized, e.g. from about 0 (where no halide ion employed) to 500 g/l, in solution, more preferably from about 10 to about 400 g/l of halide ion source in the sulfonic acid solution.

In addition to the metal salts, aqueous acid electrolytes of the invention optionally may contain a variety of other components commonly known in the electrodeposition industry. These components are often referred to as additives such as suppressors agents, accelerator agents, leveling agents and the like. The use of a buffering agent in combination with a suppressor agent, an accelerator or brightener additive is particularly preferred and provides surprisingly enhanced plating performance, particularly in hard to plate features.

A buffering agent may be used with the sulfonic acids of this invention. The buffering agent regulates the pH during electrolysis. Examples of suitable buffering agents include monocarboxylic, dicarboxylic and tricarboxylic acid such as citric acid, tartaric acid, potassium sodium tartrate, amino acids, oxalic acid, nitrogen-containing carboxylic acids and phosphonic acids. Preferred is boric acid.

Useful brighteners include those of the following formula:

$XO_3S-R-SH$ $XO_3S-R-S-S-R-SO_3X$ and $XO_3-Ar-S-S-Ar-SO_3X$ where in the above formulae R is an optionally substituted alkyl group, and preferably is an alkyl group having from 1 to 6 carbon atoms, more preferably is an alkyl group having from 1 to 4 carbon atoms; Ar is an optionally substituted aryl group such as optionally substituted phenyl or naphthyl; and X is a suitable counter ion such as ammonium, sodium or potassium. Some specific suitable brighteners include e.g. n,n-dimethyl-dithiocarbamic acid-(3-sulfopropyl)ester; 3-mercaptopropylsulfonic acid-(3-sulfopropyl)ester; 3-mercaptopropylsulfonic acid (sodium salt); carbonic acid-dithio-o-ethylester-s-ester with 3-mercapto-1-propane sulfonic acid (potassium salt); bissulfopropyl disulfide; 3-(benzthiazolyl-s-thio)propyl sulfonic acid (sodium salt); pyridinium propyl sulfobetaine; 1-sodium-3-mercaptopropane-1-sulfonate; sulfoalkyl sulfide compounds disclosed in U.S. Pat. No. 3,778,357; the peroxide oxidation product of a dialkyl amino-thiox-methyl-thioalkanesulfonic acid; and combinations of the above. Additional suitable brighteners are also described in U.S. Pat. Nos. 3,770,598, 4,374,709, 4,376,685, 4,555,315, and 4,673,469, all incorporated herein by reference. Particularly preferred brighteners for use in the plating compositions of the invention are n,n-dimethyl-dithiocarbamic acid-(3-sulfopropyl)ester and bis-sodium-sulfonopropyldisulfide.

Surfactants useful in the present invention include e.g. amines such as ethoxylated amines, polyoxyalkylene amines and alkanol amines; amides; polyglycol-type wetting agents, such as polyethylene glycols, polyalkylene glycols and polyoxyalkyene glycols; high molecular weight polyethers; polyethylene oxides (mol. wt. 100,000 to 3 million); block copolymers of polyoxy-alkyenes; alkylpolyether sulfonates; complexing surfactants such as alkoxylated diamines; Particularly suitable surfactants for plating compositions of the invention are commercially available polyethylene glycol copolymers, including polyethylene glycol copolymers.

Wetting agents may be used with the sulfonic acids of this invention. The wetting agents may be selected from cationic, anionic or non-ionic molecules.

The invention may also use complexing agents for metals particularly if the sulfonic acid of the invention is used in electrodeposition or de-scaling processes. Examples of suitable complexing agents include monocarboxylic, dicarboxylic and tricarboxylic acid such as citric acid, tartaric acid, potassium sodium tartrate, amino acids, particularly glycine, oxalic acid, alklylamines, alkylalkanol amine, EDTA and phosphonic acids.

Electrochemical processes of the invention may be carried out from less than ambient temperatures to elevated temperatures. Preferably, the electrochemical processes are used from about −20° C. to above 95° C. depending upon the processes in use.

The sulfonic acid solution may be stagnant or is preferably agitated during use such as by using an air sparger, physical movement of the work piece, ultrasonic radiation, impingement or other suitable methods.

Electrolysis is preferably conducted at a current density ranging from less than 0.1 to 3000 amperes per square foot (ASF) depending upon the process and the electrolyte characteristics.

Electrolysis times may range from about less than one minute to greater than twenty-four hours or more, depending on the difficulty of the work piece and the desired finish.

The invention described also includes the use of direct, pulse or periodic current waveforms to effectively produce a commercially acceptable metal or polymer coating.

The invention described may also use a soluble or an insoluble or inert electrode material.

A wide variety of substrates may be electroplated, descaled or coated with a conductive polymer with the compositions of the invention, as discussed above. The compositions of the invention are particularly useful to electroplate difficult work pieces, such as circuit board substrates with small diameter and low aspect vias or through-holes, integrated circuits with low aspect ratio vias, integrated circuits with high aspect ration microvias and other electronic features. The plating compositions of the invention also will be particularly useful for plating integrated circuit devices, such as formed semiconductor devices and the like. The sulfonic acids of this invention will also be useful for the de-scaling of metals. The sulfonic acids of this invention will also be useful as an electrolyte in batteries and other energy storage devices and during the polymerization of organic monomers to form conductive polymers.

The foregoing description of the invention is merely illustrative thereof, and it is understood that variations and modifications can be effected without departing from the scope or spirit of the invention as set forth in the following claims.

Example 1

A. Commercially available 70% methanesulfonic acid (MSA) that contains a high concentration of methylmethanethiosulfonate, [MMTS, $(CH_3SO_2SCH3)$] was purified by the following procedure:
(1) 250 ml of 70% methanesulfonic acid containing 12 parts-per-million (ppm) was placed into a 500 ml beaker.
(2) 30% hydrogen peroxide solution, 1.125 grams, was added and the MSA was heated to 140 degrees Fahrenheit for three hours.
(3) The methanesulfonic acid solution was cooled to room temperature and analyzed for MMTS.

The concentration of MMTS after the hydrogen peroxide treatment was non-detectable by gas chromatography methods. After purification the MSA was diluted to 15% by the addition of water.

B. A sample of 15% methanesulfonic acid (MSA) made according to Example 1A was electrolyted using a pure tin anode, an insoluble iridium oxide-coated titanium cathode. During electrolysis, tin dissolved into the 15% MSA. Trichloromethylmethylsulfone (TCMS) was added incrementally and the headspace gas above the electrochemical cell was smelled for detectable odor. After about 0.9 ppm of TCMS was added, an odor was noticeable.

Example 2

A sample of 15% methanesulfonic acid (MSA) made as in Example 1(A) was electrolyted using a pure tin anode, an insoluble iridium oxide-coated titanium cathode.

During electrolysis, tin dissolved into the 15% MSA. Methylmethanethiosulfonate (MMTS) was incrementally added and the headspace gas above the electrochemical cell was smelled for detectable odor. After about 0.25 ppm of MMTS was added, an odor was noticeable. MMTS was seen to decompose using chromatographic techniques to primarily dimethyldisulfide (DMDS) in the electrolysis cell. Methylmercaptan ($CH_3SH$) and dimethylsulfide (DMS) were also observed after electrolysis, both odorous impurities.

Example 3

A sample of 15% methanesulfonic acid (MSA) made as in Example 1(A) was electrolyted using a pure tin anode, an insoluble iridium oxide-coated titanium cathode.

During electrolysis, tin dissolved into the 15% MSA. Methylmethanethiosulfonate (MMTS) was incrementally added up to 0.85 ppm. An odor was detectable. To this solution was added 1.0 ppm of Trichloromethylsulfone (TCMS). A very pungent odor was observed indicating a synergy between the two impurities in producing the undesirable odor.

Example 4

A sample of 15% methanesulfonic acid (MSA) made as in Example 1(A) was electrolyted using a pure tin anode, an insoluble iridium oxide-coated titanium cathode.

During electrolysis, tin dissolved into the 15% MSA. Trichloromethylsulfone (TCMS) was added and after electrolysis, the MSA in the electrolysis cell contained dimethylsulfide and dimethyldisulfide leading to an undesirable odor.

Example 5

A sample of 15% methanesulfonic acid (MSA) made as in Example 1(A) was electrolyted using a pure tin anode, an insoluble iridium oxide-coated titanium cathode.

During electrolysis, tin dissolved into the 15% MSA. After electrolysis, the MSA contained no undersirable low-valent sulfur compounds. A similar study was done but 1 ppm of MMTS was added to the MSA and after electrolysis, an odor was detected and the analysis showed dimethylsulfide, methylsulfide, dimethyldisulfide and dimethyltrisulfide were present in the MSA.

Example 6

Two purities of methanesulfonic acid (MSA) were tested. One was commercially available 70% MSA; the other 70% MSA of the present invention which was made according to the procedure of Example 1 except that it was not diluted.

The impurities, with amounts, in each composition is as follows in Table 1:

TABLE 1

| | Weight %, ppm (unless indicated) | |
|---|---|---|
| Component ID | 70% MSA of the invention | Commercial 70% MSA |
| DMDS | 0.05 | <0.5 |
| MMS | None | |
| $DMSO_2$ | <5 | 20 |
| MCMS | 1 | 2 |
| MMTS | <1 | 10 |
| DCMS | 0.1 | <0.5 |
| TCMS | None | 2 |
| Other Unknowns (total) | <1 | 4 |

A zinc methanesulfonate solution was prepared by dissolving zinc carbonate in 70% methanesulfonic acid as listed above. The final concentration of zinc ion was 65 g/l. During dissolution of zinc in the impure 70% MSA, a pungent odor was observed while the zinc solution prepared using the clean 70% MSA emitted no significant odor. An additional 1 molar free MSA was added to each zinc methanesulfonate solution, the same 70% MSA that was used to prepare the zinc electrolyte. Electrodeposition of zinc from each solution was done on clean steel panels at 60 amperes per square foot (ASF). The zinc deposit plated from the clean 70% MSAS electrolyte was matte gray and uniform while the zinc deposit plated from the impure 70% zinc solution was dark, rough and commercially unacceptable.

Example 7

A stock solution of MSA 70% containing low levels of MMTS and TCMS impurities was prepared by treatment of a commercial Arkema-Mourenx Electronic Grade MSA 70% with hydrogen peroxide. After peroxide treatment, the MMTS and TCMS levels were minimal (MMTS<30 ppb, TCMS<400 ppb).

Two 500-mL electroplating cells (Hull cells) were modified to allow operation under "enclosed" conditions so as to allow testing of headspace gases. Tin metal anodes and iridium oxide coated titanium cathodes were used. In each Hull cell, a 15% aqueous solution of the MSA containing no measurable MMTS or TCMS (i.e., <0.05 ppm) was charged and N$_2$ gas flow (700 mL/min) was started to the headspace above the MSA solution. Current (2.0 A) was applied at the anode and cathode via a rectifier/power supply such that a steady stream of hydrogen bubbles formed at the cathode via the reaction Sn$^0$+2CH$_3$SO$_3$H⇌Sn(O$_3$SCH$_3$)$_2$+H$_2$. Using this assembly and operating under conditions similar to those commonly employed in SMS manufacture and in tin electroplating from SMS/MSA electrolyte, any volatile materials formed were swept from the headspace and into an outlet port. The outlet gas was then smelled by an odor panel of 4-6 people and rated for smell characteristic and intensity.

In that odor perception levels and relative intensities are highly variable between individuals, the testing procedure involved a panel of 5-6 individual who smelled the gases venting from the exit port. The two cells were operated in parallel, one serving as the test cell (with variable amounts of added MMTS or TCMS) and the second as the reference cell (no added MMTS or TCMS). The sampling cell was tested for odor prior to passing current, then initially with current. After these initial checks, a small measured amount of MSA containing MMTS and/or TCMS was injected into the test cell and the odor sampled by a panel. The injected compounds were increased in concentration until a very strong odor was noted by most panelists. To minimize desensitization effects, about ten minutes passed between repeat testing by any individual panelist. The order of panel members doing the sampling was varied. The responses of the panel were categorized/scored as follows.

0=no difference between reference and sampling cell
1=barely detectable difference
2=definite difference
3=strong unpleasant odor.

The odor threshold for each composition was then defined as the concentration(s) in the electrolysis bath of added MMTS and/or TCMS where half or more of the panelist scored the odor of the composition as "1" or higher. The collated odor thresholds for these tests with MMTS and TCMS are tabulated below in Table 2.

TABLE 2

Impurity Odor Thresholds in Electrolytic Sn - MSA systems

| Impurity Concentration in 15% MSA in Test | | Equivalent Concentration in 70% MSA | |
|---|---|---|---|
| MMTS ppb | TCMS ppb | MMTS ppm | TCMS ppm |
| 380 | 0 | 1.8 | 0.0 |
| 73 | 400 | 0.34 | 1.9 |
| 50 | 1300 | 0.23 | 6.1 |
| 0 | 5300 | 0.00 | 25 |

The invention claimed is:

1. An aqueous solution for use in an electrochemical process, the solution comprising a sulfonic acid, trichloromethyl methyl sulfone and methyl methanethiosulfonate wherein said trichloromethyl methyl sulfone is present in amounts less than about 6 parts per million, and said methyl methanethiosulfonate is present in amounts less than about 0.25 parts per million.

2. The solution of claim 1 for use in electrodeposition, batteries, conductive polymers and descaling processes.

3. The solution of claim 1 wherein the sulfonic acid is derived from an alkyl monosulfonic acid, an alkyl polysulfonic acid or an aryl mono or polysulfonic acid.

4. The solution of claim 1 wherein the sulfonic acid is:

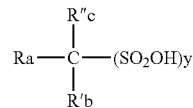

wherein a+b±c+y equals 4, R, R' and R" are the same or different and each independently are hydrogen, phenyl, Cl, F, Br, I, CF$_3$ or a lower C$_{1-9}$ alkyl group that is unsubstituted or substituted by oxygen, Cl, F, Br, I, CF$_3$, or —SO$_2$OH.

5. The solution of claim 4 wherein the sulfonic acid is selected from the group consisting of methanesulfonic acid, ethanesulfonic acid, propanesulfonic acid, methanedisulfonic acid, monochloromethanedisulfonic acid, dichloromethanedisulfonic acid, 1,1-ethanedisulfonic acid, 2-chloro-1,1-ethanedisulfonic acid, 1,2-dichloro-1,1-ethanedisulfonic, acid, 1,1-propanedisulfonic acid, 3-chloro-1,1-propanedisulfonic acid, 1,2-ethylene disulfonic acid, 1,3-propylene disulfonic acid, trifluormethanesulfonic acid, butanesulfonic acid, perfluorobutanesulfonic acid, pentanesulfonic acid, phenylsulfonic acid, phenolsulfonic acid, para-toulenesulfonic acid, xylenesulfonic acid and mixtures thereof.

6. The solution of claim 4 wherein the sulfonic acid is a free alkanesulfonic acid having a concentration range from 1 to 1480 g/l.

7. The solution of claim 6, wherein the concentration of the free alkanesulfonic acid is about 10 to about 700 grams per liter of solution.

8. The solution of claim 6, wherein the concentration of the free alkanesulfonic acid is about 30 to about 500 grams per liter of solution.

9. The solution of claim 1 wherein the pH is between −2 to 13.

10. The solution of claim 1 further comprising inorganic or organic acids in combination with said sulfonic acid.

11. The solution of claim 1 further comprising a metal sulfonate salt or other metal salts and free sulfonic acids.

12. The solution of claim 11 wherein the other metal salts is a salt of an alkyl or aryl sulfonic acid of formula:

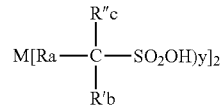

wherein a+b±c+y equals 4, M is a metal selected from metals in Group 1B, 2B, 3A, 3B, 4A, 4B, 5A, 5B, 6B, 7B, 8B, lanthanide metals of the periodic table, of actinide metals of the periodic table, ammonium ion or mixtures thereof, R, R' and R" are the same or different and each independently is hydrogen, phenyl, Cl, F, Br, I, CF$_3$ or a C$_{1-23}$ alkyl group that is unsubstituted or substituted by oxygen, Cl, F, Br, I, CF$_3$, or —SO$_2$OH.

13. The solution of claim 11 wherein the metal sulfonate salt or other metal salts are present at a concentration froth about 1 to about 600 grams per liter of aqueous solution.

14. The solution of claim 11 wherein the free sulfonic acids are selected from the group consisting of methanesulfonic acid, ethanesulfonic acid, propanesulfonic acid, trifluoromethanesulfonic acid and mixtures thereof.

15. The solution of claim 11 wherein the metal sulfonate salt or other metal salts is selected from metals in Group 1B, 2B, 3A, 3B, 4A, 4B, 5A, 5B, 6B, 7B, 8B, lanthanide or actinide metals of the periodic table and ammonium ion or mixtures thereof.

16. The solution of claim 11 wherein the metal sulfonate salt or other metal salts is zinc methanesulfonate salt.

17. The solution of claim 11 wherein the metal sulfonate salt or other metal salts is copper methanesulfonate salt.

18. The solution of claim 11 wherein the metal sulfonate salt or other metal salts is nickel methanesulfonate salt.

19. The solution of claim 11 wherein the metal sulfonate salt or other metal salts is ferrous methanesulfonate salt.

20. The solution of claim 11 wherein the metal sulfonate salt or other metal salts is an alkali or alkaline earth metal salt.

21. The solution of claim 11 wherein the metal sulfonate salt or other metal salts is a mixture of metal sulfonate salts selected from metals in Group 1B, 2B, 3A, 3B, 4A, 4B, 5A, 5B, 6B, 7B, 8B, lanthanide and actinide metals of the periodic table and ammonium ion.

22. The solution of claim 1 further comprising a buffering agent to modulate the pH of the aqueous solution.

23. The solution of claim 22 wherein the buffering agent is boric acid.

24. The solution of claim 1 further comprising an organic monomer selected from aniline or substituted aniline or pyrrole.

* * * * *